United States Patent
Godavarty

(10) Patent No.: US 10,674,916 B2
(45) Date of Patent: Jun. 9, 2020

(54) INTEGRATED NIR AND VISIBLE LIGHT SCANNER FOR CO-REGISTERED IMAGES OF TISSUES

(71) Applicant: Anuradha Godavarty, Miami, FL (US)

(72) Inventor: Anuradha Godavarty, Miami, FL (US)

(73) Assignee: The Florida International University Board of Trustees, Miami, FL (US)

(*) Notice: Subject to any disclaimer, the term of this patent is extended or adjusted under 35 U.S.C. 154(b) by 0 days.

(21) Appl. No.: 15/645,677

(22) Filed: Jul. 10, 2017

(65) Prior Publication Data
US 2019/0008387 A1 Jan. 10, 2019

(51) Int. Cl.
| A61B 5/00 | (2006.01) |
| A61B 5/1455 | (2006.01) |
| A61B 5/026 | (2006.01) |
| G06T 7/00 | (2017.01) |
| G06T 7/62 | (2017.01) |
| H04N 5/225 | (2006.01) |

(Continued)

(52) U.S. Cl.
CPC .......... *A61B 5/0035* (2013.01); *A61B 5/0013* (2013.01); *A61B 5/0077* (2013.01); *A61B 5/0261* (2013.01); *A61B 5/14552* (2013.01); *A61B 5/445* (2013.01); *A61B 5/7203* (2013.01); *A61B 5/7435* (2013.01); *G06T 7/0012* (2013.01); *G06T 7/62* (2017.01); *G06F 3/04817* (2013.01); *G06T 7/11* (2017.01); *G06T 7/60* (2013.01); *G06T 2207/10048* (2013.01); *G06T 2207/30088* (2013.01); *G06T 2207/30096* (2013.01); *G06T 2207/30104* (2013.01); *H04N 5/2256* (2013.01)

(58) Field of Classification Search
CPC ... A61B 5/0059; A61B 5/0035; A61B 5/7435; A61B 5/0077; A61B 5/445; A61B 5/7203; A61B 5/0013; A61B 5/14552; A61B 5/0261; H04N 5/2256; G06F 3/04817; G06T 2207/30096; G06T 2207/30104; G06T 7/60; G06T 7/11
See application file for complete search history.

(56) References Cited

U.S. PATENT DOCUMENTS

| 7,715,705 B2 * | 5/2010 | Yasutomi | G03B 15/02 348/371 |
| 8,712,504 B2 | 4/2014 | Godavarty et al. | |

(Continued)

OTHER PUBLICATIONS

Jarbrink et al., "Prevalence and incidence of chronic wounds and related complications: a protocol for a systematic review," Systematic Reviews, Sep. 2016, pp. 1-6, vol. 5, No. 152.

(Continued)

*Primary Examiner* — Peter Luong
(74) *Attorney, Agent, or Firm* — Saliwanchik, Lloyd & Eisenschenk

(57) ABSTRACT

Systems and methods for scanning near infrared (NIR) and visible light images and creating co-registered images are provided. A system can include a visible light image capturing device, an near infrared image capturing device, a housing unit, a light source configured to emit light at multiple wavelengths, and a processor configured to use image segmentation algorithms to measure a target issue or wound, detect hemodynamic signals, and combine the visible light image and a hemodynamic image to create a single image.

19 Claims, 13 Drawing Sheets

(51) Int. Cl.
G06T 7/11 (2017.01)
G06T 7/60 (2017.01)
G06F 3/0481 (2013.01)

(56) References Cited

U.S. PATENT DOCUMENTS

| | | | |
|---|---|---|---|
| 9,635,649 | B1 | 4/2017 | Amiri et al. |
| 2007/0060809 | A1* | 3/2007 | Higgins ............... A61B 5/0075 600/328 |
| 2008/0292164 | A1* | 11/2008 | Azar .................... A61B 5/0091 382/131 |
| 2010/0190061 | A1 | 7/2010 | Green |
| 2011/0184295 | A1* | 7/2011 | Orbach .................... A61B 5/00 600/504 |
| 2012/0078088 | A1* | 3/2012 | Whitestone .......... A61B 5/0077 600/425 |
| 2013/0150687 | A1* | 6/2013 | Kato .................. A61B 5/14551 600/324 |
| 2014/0364743 | A1 | 12/2014 | Godavarty et al. |
| 2015/0190061 | A1* | 7/2015 | Godavarty ......... A61B 5/02028 600/328 |

OTHER PUBLICATIONS

Alavi et al., "What's new: management of venous leg ulcers—treating venous leg ulcers," Journal of American Academy of Dermatology, Apr. 2016, pp. 643-664, vol. 74, No. 4.
Steed et al., "Guidelines for the treatment of diabetic ulcers," Wound Repair and Regeneration, Nov. 2006, pp. 680-692, vol. 14.
Neidrauer et al., "Near infrared wound monitor helps clinical assessment of diabetic foot ulcers," Journal of Diabetes Science and Technology, Jul. 2010, pp. 792-798, vol. 4, No. 4.
Weingarten et al., "Prediction of wound healing in human diabetic foot ulcers by diffuse near-infrared spectroscopy: a pilot study," Wound Repair and Regeneration, Mar. 2010, pp. 180-185, vol. 18.
Schreml et al.,"Oxygen in acute and chronic wound healing," British Journal of Dermatology, Apr. 2010, pp. 1-12.
Godavarty et al., "Diabetic wound imaging using a noncontact near-infrared scanner: a pilot study," Journal of Diabetes Science and Technology, Jun. 2015, pp. 1158-1159, vol. 9, No. 5.
"Advanced wound care and closure market overview," Advanced Wound Care and Closure Market (Types, Applications, End User and Geography), Jul. 2014, pp. 1-3, https://www.alliedmarketresearch.com/wound-closure-wound-care-market.
Jung et al., "Functional near-infrared imaging reconstruction based on spatiotemporal features: venous occlusion studies," Applied Optics, Apr. 2015, pp. D82-D90, vol. 54, No. 13.
Jung et al., "Portable wide-field hand-held NIR scanner," SPIE Advanced Biomedical and Clinical Diagnostic Systems, Mar. 2013, pp. 1-9.
Jung et al., "Anatomical co-registration using spatio-temporal features of a non-contact near-infrared optical scanner," SPIE Dynamics and Fluctuations in Biomedical Photonics, Feb. 2014, pp. 1-6.
Jung et al., "Spatio-temporal hemodynamic imaging using non-contact NIR scanner (NIROS)," Biomedical Optics, Apr. 2014, pp. 1-3.
Godavarty et al., "Non-contact optical imaging of healing and non-healing diabetic foot ulcers," SOUE Optical Biopsy XIII: Toward Real-Time Spectroscopic Imaging and Diagnosis, Mar. 2015, pp. 1-4, Author Copy.
Lei et al., "Quantitative wound healing studies using a portable, low-cost, hand-held near-infrared optical scanner: preliminary sensitivity and specificity analysis," SPIE Optics and Biophotonics in Low-Resource Settings II, Mar. 2016, pp. 1-6, vol. 9699.
Dadkhah et al., "Wound size measurement of lower extremity ulcers using segmentation algorithms," SPIE Optical Biopsy XIV: Toward Real-Time Spectroscopic Imaging and Diagnosis, Mar. 2016, pp. 1-6, Author Copy.
Pang et al., "Near-infrared optical imaging and wound segmentation in lower extremity ulcers," Clinical and Translational Biophotonics, Apr. 2016, pp. 1-3.

* cited by examiner

INTEGRATED NIR AND VISIBLE LIGHT SCANNER FOR CO-REGISTERED IMAGES OF TISSUES

BACKGROUND

Chronic wounds affect approximately 6.5 million Americans and the incidence is expected to rise by 2% annually over the next decade, due to aging population, diabetes, obesity, and late effects of radiation therapy. Among the major chronic wounds are lower extremity ulcers (diabetic foot ulcers (DFUs) and venous leg ulcers (VLUs)), apart from pressure and arterial ulcers. The global wound care market is expected to reach $20.5 billion by 2020 at a cumulative annual growth rate of 8%, and just North America alone to $8.1 billion by 2020. Chronic wounds alone are responsible for over $7 billion/year in annual health care costs worldwide. The United States represents more than half the global market with lower extremity ulcers (DFUs and VLUs) being the most chronic wounds.

Initial management of lower extremity ulcers begins with effective clinical assessment of the wound, diagnostic imaging using duplex ultrasound (to assess vascularity, or extent of blood flow), followed by basic and/or advanced treatments (or therapies) for enhancing effective and rapid wound healing. Healing rate is assessed by wound size measurement and visual assessment for surface epithelization. If treatment extends beyond 4 weeks, re-evaluation of wound and advanced treatment options are considered. While currently available diagnostic tools help direct the treatment approach and assess vascularity (i.e., oxygen-rich blood flow), there is no prognostic imaging tool in the clinic to assess improvement in blood oxygenation and simultaneously take spatial measurements of a target wound.

BRIEF SUMMARY

Embodiments of the subject invention provide devices and methods for scanning near infrared (NIR) and visible light images of targeted wounds through non-invasive, non-contact, prognostic imaging tools that provide mapping changes in blood oxygenation of the wound region and obtaining wound size measurements. Embodiments of the subject invention provide non-contact and real-time NIR imaging of the entire wound region in less than or equal to one second of imaging time.

Embodiments of the subject invention can use visible light capturing devices and NIR capturing devices to scan target tissues or wounds, obtain wound size measurements and/or measurements of chosen regions of interest, through automated wound or region of interest's boundary demarcation, and map blood oxygenation changes in small and large tissues or wounds to provide separate healing indicators in a single co-registered image.

Embodiments of the subject invention provide systems and methods to create a co-registered image by overlaying a hemodynamic map onto a visible light image. In some embodiments, software can provide spatially co-registered hemodynamic and color images of a tissue, wound, region of interest and their peripheries, along with automated tissue, wound, or region of interest boundary demarcation and wound size measurement.

BRIEF DESCRIPTION OF DRAWINGS

FIG. 12A shows the first part of the diagram; FIG. 12B is a continuation from FIG. 12A, showing the next part of the diagram; and FIG. 12C is a continuation from FIG. 12B, showing the last part of the diagram.

DETAILED DESCRIPTION

Figure 1:
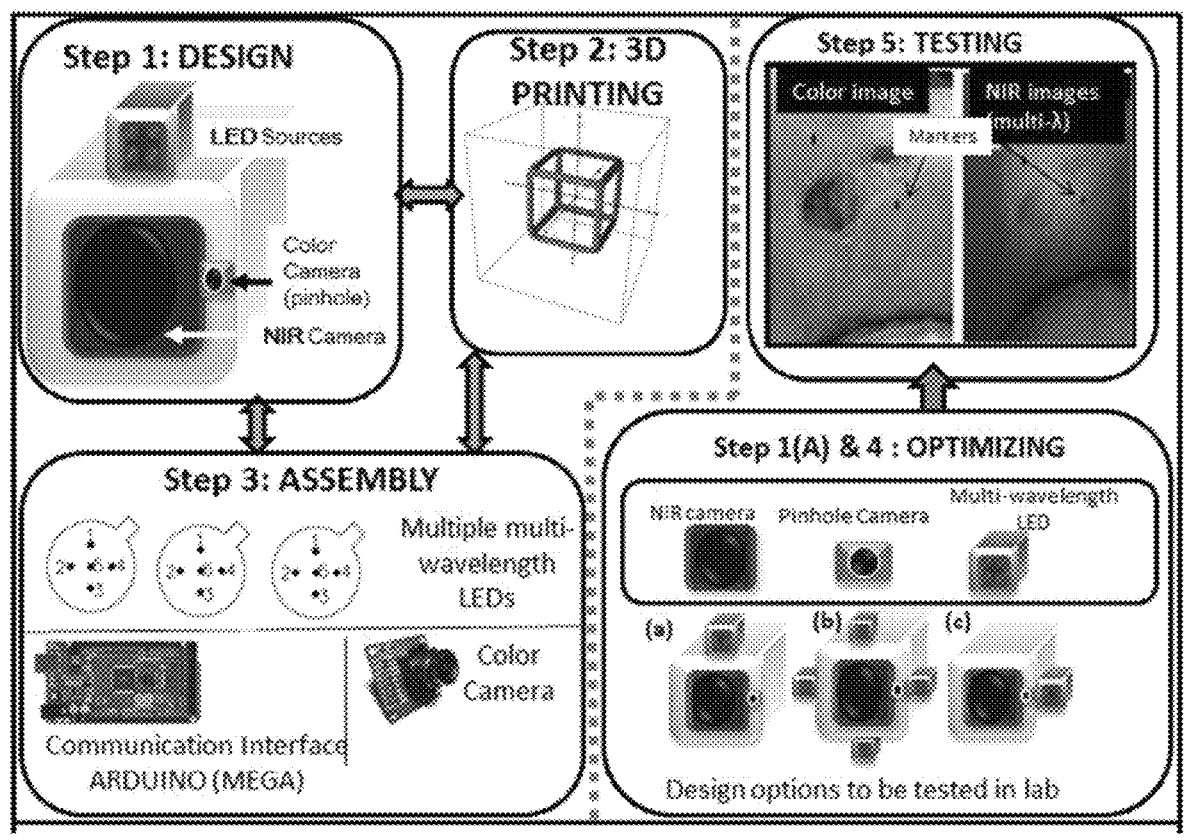
FIG. 1 shows a process flow for fabricating an integrated near infrared (NIR) and light imaging scanner according to an embodiment of the subject invention.

Embodiments of the subject invention (at times referred to as the NIROScope) provide devices and methods for a prognostic optical imaging tool to monitor changes in blood flow of chronic wounds (e.g., lower extremity ulcers) and determine of wound size during the treatment process. It should be understood that the term "hemodynamic signals," as used herein, can include or be used interchangeably with oxygenation parameter, blood oxygenation, tissue oxygenation, changes in oxy and deoxy hemoglobin or related parameters obtained from multi wavelength NIR data. It should be further understood that the term "visible light" can include visual light, white light, or digital color.

Near infrared spectrometry (NIRS) is a vibration based spectrometry method that propagates electromagnetic waves within a range of 650 nm to 2500 nm and records the induced signal response. NIRS is advantageous when probing the human body as it is non-destructive, non-invasive, and fast with typical exposure time lasting less than a few minutes. Typical applications for NIRS include detecting neural activity, pulse oximetry, or analyzing biological tissue. Typical NIRS instruments vary based upon a desired application and wavelength selectivity, and typically fall into dispersive, filter, Fourier transform, LED, or Acousto-Optical Tunable Filter based instruments.

Optical imaging modalities can image tissue functionality in terms of changes in blood flows (or oxygenation) and perfusion. Optical imaging devices can use light in the visible or near infrared light wavelengths to monitor changes in the blood flow in terms of oxy-(HbO), deoxyhemoglobin (HbR), oxygen saturation ($StO_2$), total hemoglobin (HbT), and/or tissue perfusion of the wounds. Wounds undergo different stages of healing, including: inflammatory, proliferation, and remodeling. While healing wounds progress through all these stages towards complete closure, non-healing wounds remain at the inflammatory phase with stagnated blood (i.e. no blood flow or blood oxygenation). Hence, differences in blood oxygenation between wound and normal tissue, when optically imaged, can help determine the wound's responsiveness to the treatment process and progression towards healing.

Embodiments of the subject invention can obtain wound size measurements (via automated or semi-automated wound boundary demarcations) and map blood oxygenation changes in small and large wounds (up to ~8 cm in one dimension) to provide two healing indicators in a single co-registered image. Other embodiments of the subject invention can demarcate and measure the size of regions with changed blood-oxygenation in and around the wounds.

Key advantages of embodiments of the subject invention include: (1) portability; (2) non-contact; (3) non-destructive; (4) ability to image small & large wounds (greater than 4 cm in a single dimension); (5) non-invasive (for example, no injection of contrast agents); (6) measurement of changes in blood oxygenation around wound (in terms of $StO_2$, HbO, and HbR); and (7) operator independence for wound size measurements.

Embodiments of the subject invention provide devices and methods for a non-invasive, non-contact, prognostic imaging tool to provide two healing indicators: (1) mapping changes in blood oxygenation of the wound region; and (2) obtaining wound size measurements. Embodiments of the subject invention provide non-contact and real-time NIR imaging of the entire wound region in less than or equal to one second of imaging time. The non-contact, non-radiative imaging makes the approach safe for use on subjects with infectious, non-infectious, painful, and/or sensitive wounds in comparison to a contact-based (using fibers) NIRS devices developed in the past. Additionally, embodiments of the subject invention can generate images of blood oxygenation of a wound of up to approximately 8 cm in one dimension in less than or equal to one second of imaging time. The imaging time of less than one second decreases the length of time of an overall prognostic assessment of healing in a routine outpatient clinical treatment.

Embodiments of the subject invention provide at least two healing indicators in one device: (1) detection of changes in blood oxygenation and/or demarcating these regions; and (2) detection of changes in wound size. Changes in two dimensional hemodynamic concentrations maps (including but not limited to changes in terms of HbO, HbR, HbT, and $StO_2$) of a wound can be detected. This can assist medical and research professionals in determining the contrast in oxygen rich blood flow into a wound, with respect to background or peripheries, and correlating these blood oxygenation changes across a specified treatment period.

In addition, embodiments of the subject invention can also obtain wound size measurements, via automatic or semi-automated segmentation methods, with no operator dependability. In an embodiment, a portable hand-held device can be mobile to any clinical site or home care service. According to some embodiments, the device can be carried along with a laptop to any clinical site or home care service during weekly treatment and assessment of the wound. In some embodiments, the hand-held nature of the device allows it to flexibly image a wound from any location with ease and from a distance of more than 30 cm or 1 ft. from the wound, without having to move the patient.

Embodiments of the subject invention can generate a spatially co-registered image, which includes both healing indicators in near-real time. The co-registered image can be created by overlaying a visible light or white light image upon a hemodynamic map or overlaying a hemodynamic map onto a visible light image. In some embodiments of the subject invention, software can provide spatially co-registered hemodynamic and color (i.e., visible light or white light) images of a wound and its peripheries, along with automated wound boundary demarcation and wound size. This can assist clinicians to correlate changes in blood oxygenation to wound size reduction across weeks of treatment from visual yet scaled co-registered images. In some embodiments of the subject invention, software can provide spatially co-registered demarcated boundaries of changed blood oxygenation (or hemodynamic maps) from a wound and its peripheries, along automated wound boundary demarcation (from visible light image) and wound size. This can assist clinicians to correlate changes in blood oxygenation to wound size reduction across weeks of treatment from quantitatively scaled, co-registered demarcated boundaries and sizes (as area).

Embodiments of the subject invention can assess changes in blood flow (from hemodynamic wound maps) along with wound size measurements to potentially predict healing sooner than traditional benchmark approaches of measuring wound size; as physiological changes in the wound manifest prior to visually perceptible changes. In an embodiment, two healing indicators can be used to assess the effectiveness of the treatment approach and determine if oxygenation to the wound is impacted by a chosen treatment. By allowing clinicians to continue or alter chosen treatment plans even prior to the standard four week treatment plan (for each chosen treatment), reduction of the overall wound care costs is achieved.

Figure 13:
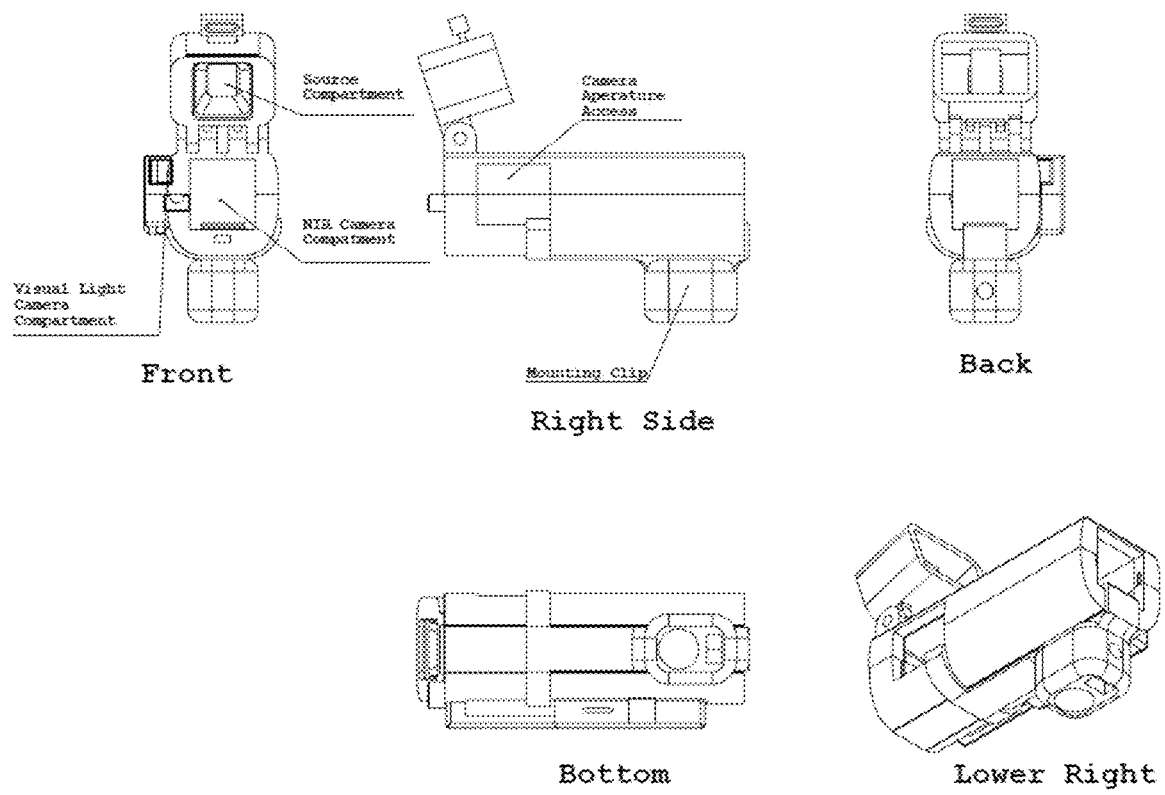
FIG. 13 shows multiple schematic views of the integrated near infrared (NIR) and light imaging scanner.

Embodiments of the subject invention (i.e., NIROScope) can comprise an image capturing device, an NIR image capturing device, a housing unit, in which the housing unit has at least one or more apertures to expose the image capturing device and the NIR image capturing device, a light source connected to the housing unit to illuminate a target region. An embodiment of the NIROScope can be seen in FIGS. 5 and 13, in which the housing unit consists of an NIR camera compartment with a front face, bottom face, right face, left face, and a back face, in which a NIR image capturing device is located inside the NIR camera compartment, in which the NIR camera is configured to receive a reflected NIR signal through an aperture at the front face of the housing unit, a source compartment to house a light generating source connected by a hinge to a top portion of the front face of compartment, in which the hinge allows the light source to move in a two dimensional direction, a visible light camera compartment connected to the NIR camera compartment, in which the visible light camera compartment houses a light image capturing device, (for example, a pinhole camera), in which the visible light capturing device is configured to receive light through an aperture at the front face of the housing unit, and a mounting clip connected to the NIR camera compartment at the bottom face and the back face, in which the mounting clip is configured to allow connection to a mount.

Figure 3:
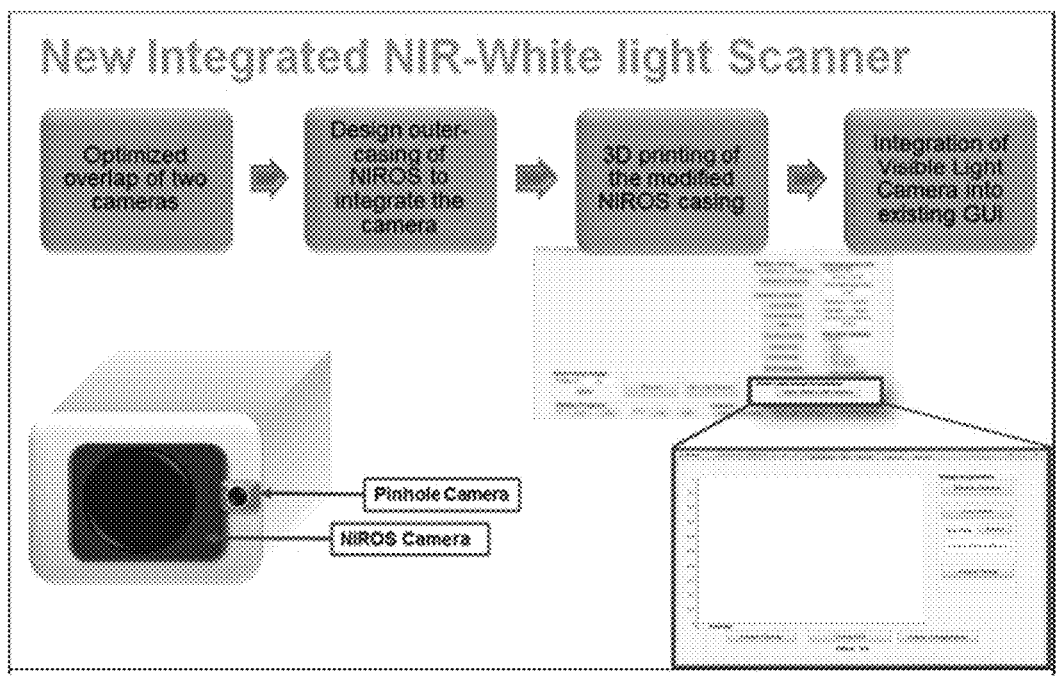
FIG. 3 shows a flow chart of an overview of a process flow for fabricating an integrated near infra-red (NIR) and white light (or visible light) scanner according to an embodiment of the subject invention.

A process for fabricating a device according to an embodiment can comprise the following, as seen in FIGS. 1 and 3: a first design step can be to place multiple multi-wavelength LEDs in various configurations and estimate the total field of view (FOV) of the source illumination (i.e. common area of illumination across all wavelengths of light). Embodiments of the subject invention can optimize different configurations of LEDs to evaluate the upper and lower limits of device's performance. Similarly, optimal positioning of an image capturing device onto the hand-held body can be determined in order to maximize the FOV overlap between the image capturing device (for color images) and NIR-sensitive camera (for multi-wavelength NIR images).

A second step can be to fabricate the housing unit, including the appropriate location(s) of the light source, a visible light capturing device, including a digital color or white light image capturing device, and the NIR image capturing device into a single integrated device with 3D printing, in addition to an area to hold the source drivers. In certain embodiments, multiple multi-wavelength LEDs can be wired to a microcontroller via custom-designed and developed printed circuit boards (PCBs) and programmed. Multi-wavelength LEDs can be used due to HbO, HbR, HbT, and/or $StO_2$ change estimations requiring diffuse reflectance signals from 2 or more NIR wavelengths. Different image capturing devices can be implemented and selected based on resolution, size, color, FOV (to match with NIR-camera), and communication requirements. Embodiments of the subject invention can be integrated onto a hand-held body and wirelessly communicate with a computer readable medium (or via a USB, if wired). A NIR image capturing device along with appropriate optical filters and focusing lens can be assembled inside the hand-held body and communicate with the computer readable medium. Certain particular embodiments can be limited to a maximum size of 5×5×12 $cm^3$ and weigh less than 1 lb., including all the assembled components.

Figure 5:
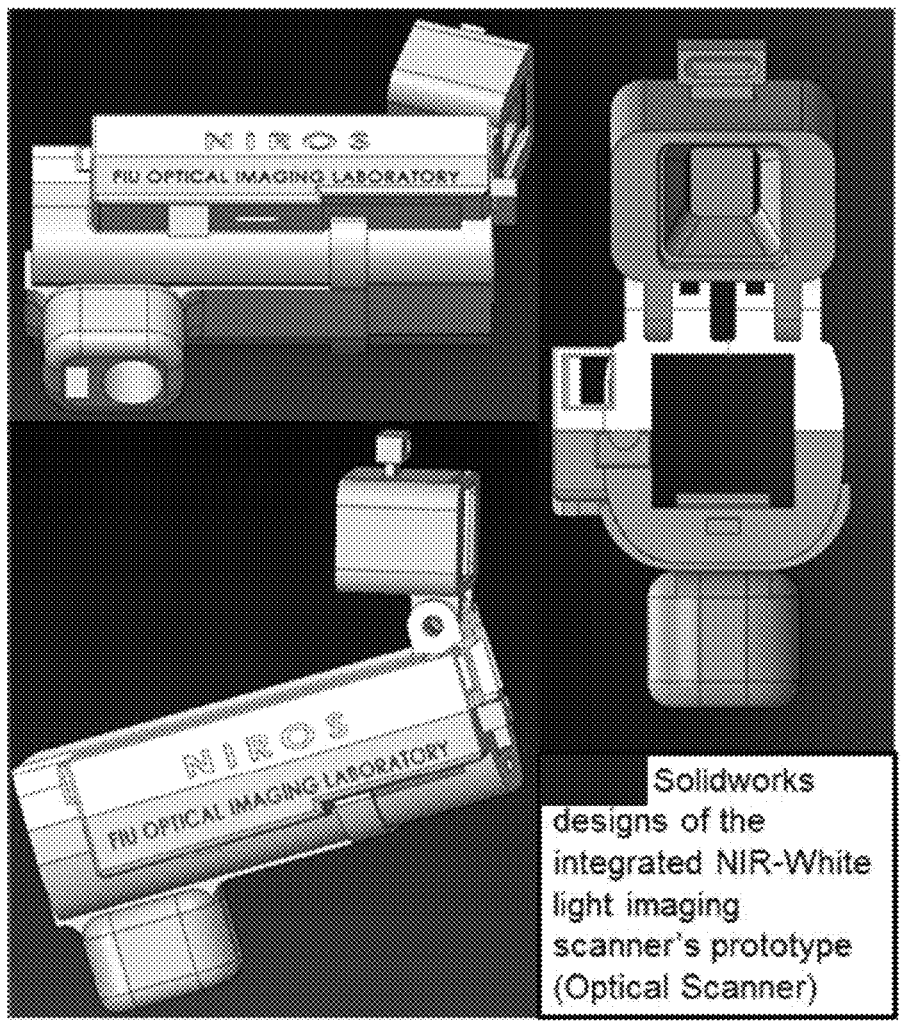
FIG. 5 shows a rendition of an integrated near infrared (NIR) and light imaging scanner according to an embodiment of the subject invention.
Figure 6:
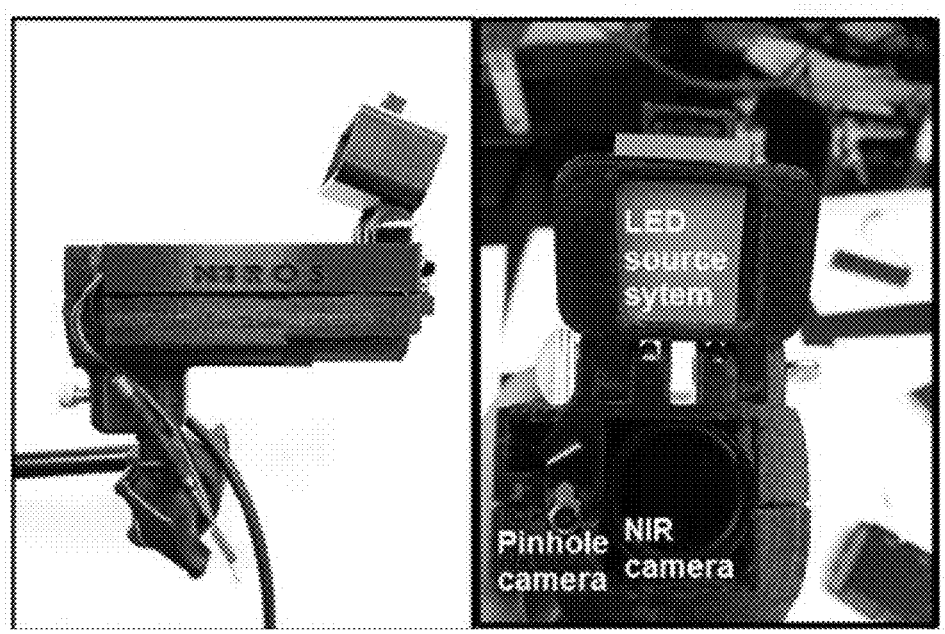
FIG. 6 shows a 3D printed integrated near infrared (NIR) and light imaging scanner according to an embodiment of the subject invention.

A fourth step can be used to perform optimization to provide uniform illumination over large areas (at chosen NIR wavelengths) with stability over time. Parameters such as changes in source light intensity vs. time, and optimal distance from device to target vs. maximum area of illumination can be analyzed according to embodiments of the subject invention. An oscilloscope and optical power meter can be used to optimize the output wavelengths and intensity at each wavelength of the LED light source. This can allow uniform intensity of illumination across wavelengths during imaging. In certain embodiments of the subject invention, any remaining non-uniformity in illumination can be accounted for using diffusers and/or calibration approaches. Variation in source illumination strength, distance and angle of view of device from wound can be accounted for and optimized according to certain embodiments of the subject invention. Dark current noise and effect of ambient light can be estimated and accounted for during data analysis. The exposure time, focal length and resolution of NIR image capturing device can also be optimized to maximize the weak diffuse reflectance signals from the wounds. FIGS. 5 and 6 include potential designs of an integrated NIR and white light (or visible light) imaging scanner according to embodiments of the subject invention.

Figure 2:
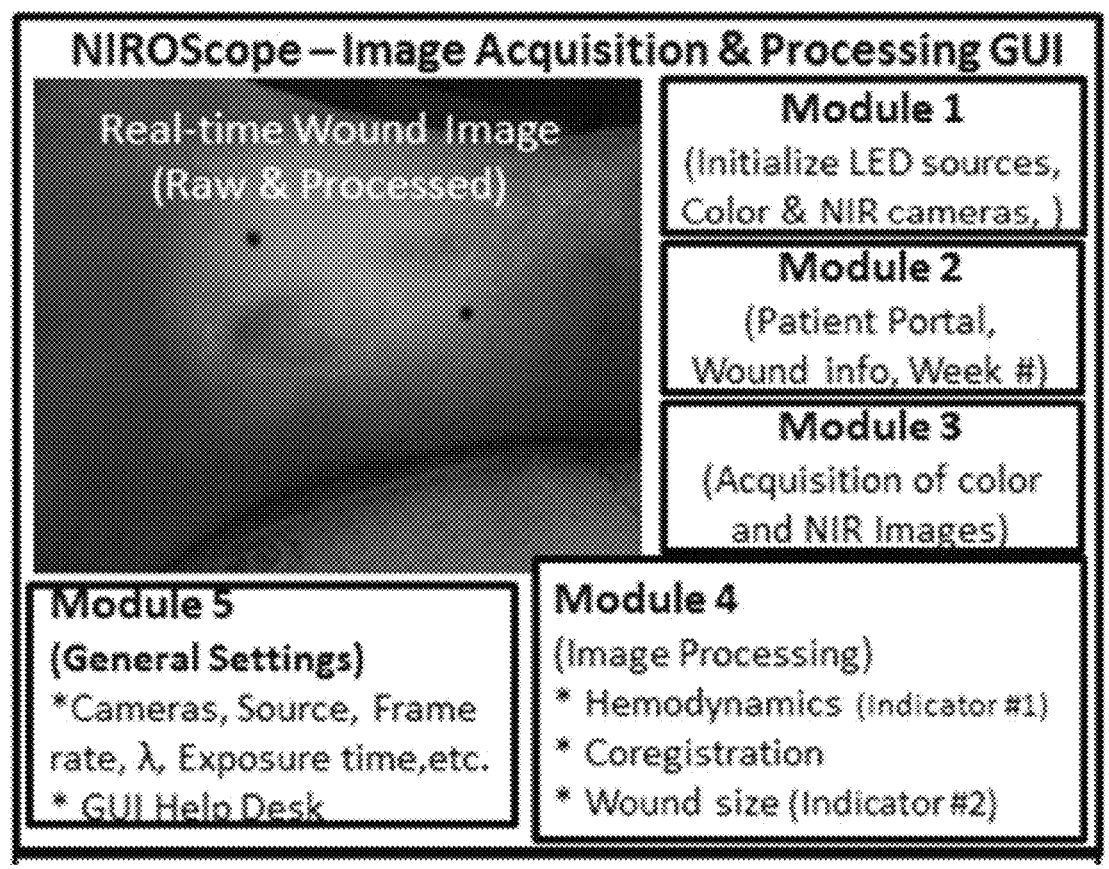
FIG. 2 shows a schematic of an image acquisition and contents of a processing graphical user interface (GUI) according to an embodiment of the subject invention.

A fifth step can be to test the fabricated device by carrying out continuous-wave (CW) NIR imaging on tissue phantoms of homogenous optical properties, followed by in-vivo analysis on normal tissue, and on lower extremity ulcers. The testing can determine the maximum FOV of illumination and detection on simulated target regions (for example, 0.5-15 cm diameter) on tissue phantoms and normal tissue. Similarly, in certain embodiments of the subject invention, the FOV of the visible image capturing device and the NIR image capturing device can be configured for various distances of the device from the target (e.g. wound or tissue). A schematic of a potential flow for fabrication of the device is seen in FIG. 3. In some embodiments, a device can be coupled with a user-friendly image acquisition and processing graphical user interface (GUI) for real-time assessment of wound's size and hemodynamics, as seen in FIG. 2. The image acquisition and processing GUI can comprise several modules, in which each module can comprise a plurality of widgets or graphical icons to allow a user to interact with the subject invention. A first module can allow a user to initialize elements of the subject invention such as the LED sources, image capturing devices and NIR image capturing devices. Embodiments of the subject invention can be configured to allow a user to delay an operation of one or more elements or allow operation for a specific period of time.

A second module can comprise a patient portal and allow a user to interact with a subject's medical records. Through interaction with the widgets or graphical icons, a user can enter a subject's case history including test results, notes, and captured images. Additionally, a user can review previously entered data in order to evaluate a subject's progress.

Figure 10:
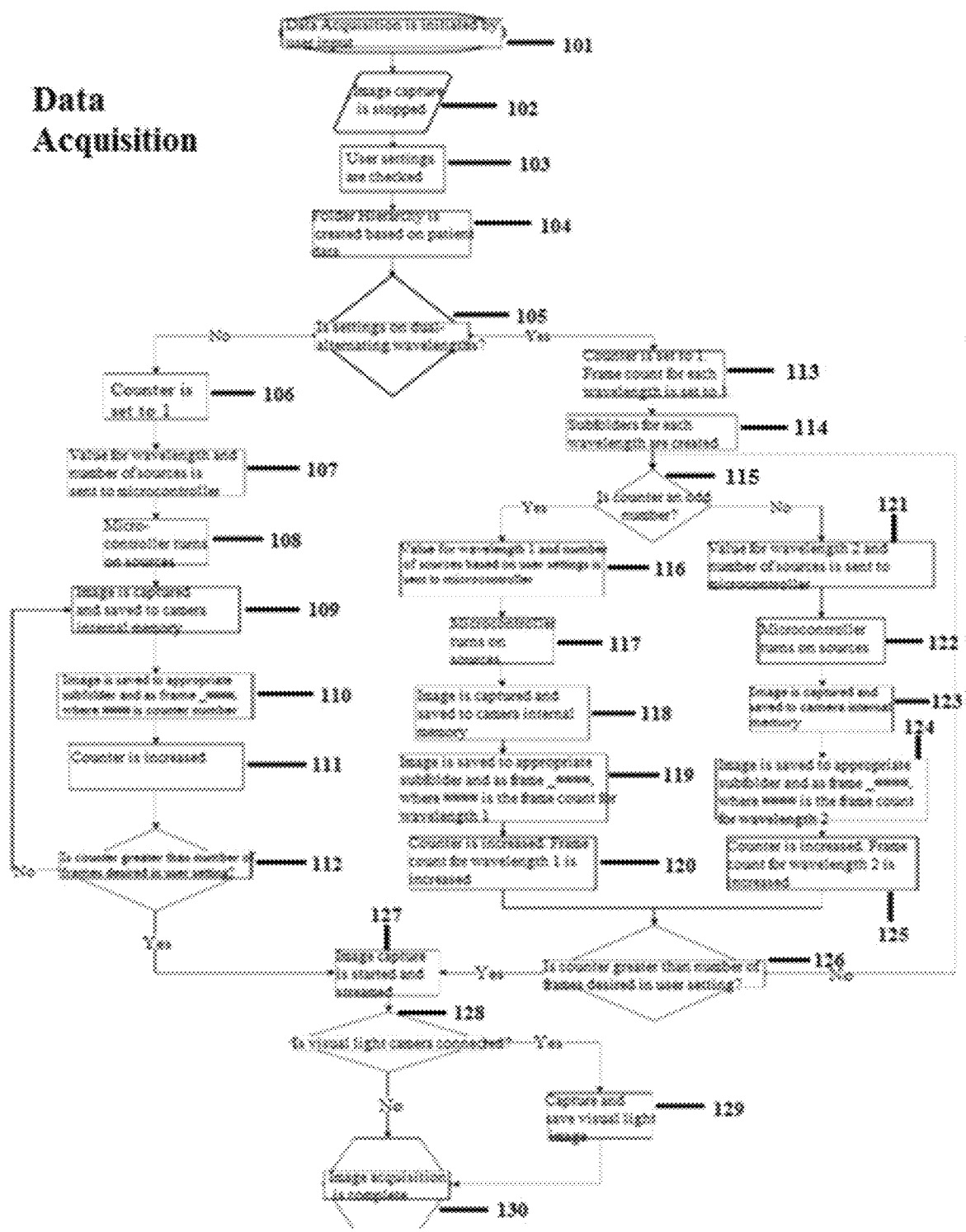
FIG. 10 shows a flow chart illustrating the process of data acquisition according to an embodiment of the subject invention.

A third module can enable a user to engage image acquisition of the color and NIR images. FIG. 10 shows a flow chart illustrating the process of data acquisition according to an embodiment of the subject invention. Within the state diagram, each state corresponds to a node. Each path is identified by an arrow, in which a path flows from one state to another state. After data acquisition is initiated 101, the image capture process can be stopped 102, user settings are checked 103 and a folder hierarchy can be created based upon an individual patient's class 105. Afterwards a decision can be made on whether or not to use dual-alternating wavelengths 105. When dual-alternating wavelengths are not used, the counter can be set to 1 106. A value for a wavelength and the number of sources can be sent to a microcontroller 107 and the microcontroller turns the sources on 108. An NIR image can be captured and stored in the memory 109 according to an embodiment of the subject invention. The retrieved NIR image can be saved in an appropriate frame number, in which the frame number can correspond to a counter number 110. Afterwards, the counter can be incrementally increased 111 and the path can be directed back to capturing and saving the NIR image in memory 109 until the desired number of frames is reached 112. An alternative path is that the setting is set for dual-alternating wavelengths, in which case the counter can set to 1 and the frame count for each wavelength can be set to 1 113. Subfolders can be created for each wavelength created 114. A next step in the process can be to determine if the value of the counter is an odd number 115. If the value of the counter is odd, the value for wavelength 1 and the number of sources can be sent to a microcontroller 116. Once the microcontroller has received the information, it can activate the appropriate sources 117. After the sources are operational, an NIR image can be captured and stored into memory 118. The NIR image can be saved to an appropriate subfolder and identified as a frame number, in which the frame number can be the frame count for wavelength 1 119. The counter can then be increased and the frame count for wavelength 1 can be increased 120. The system then determines whether the counter is greater than the number of frames desired by a user 125. If the counter is not greater than the number of frames desired, the path can be directed back to determination of whether the value of the counter is an odd number 115. After creating of subfolders for each wavelength 114 and determination of whether the counter is greater than the number of frames desired 125, a determination is made of whether the counter is an odd number 115. If the value of the counter is not an odd number, the value for wavelength 2 and the number of sources are sent to the microcontroller 121. After receiving the information, the microcontroller can turn the sources on 122. An image can be captured by an NIR image capturing device and saved to memory 123. The NIR image can be saved to an appropriate subfolder and identified as a frame number, in which the frame number can be the frame count for wavelength 2 124. The counter can then be increased and the frame count for wavelength 2 can be increased 125. A determination can be made on whether the counter is greater than the number of frames desired by the user 126. If the counter is not greater than the number of frames desired by the user, the path can be directed back to determination of whether the counter is an odd number 115. Regardless of whether or not the user setting indicated dual-alternating wavelengths 105, once the counter is greater than the number of frames desires by the user, the path is directed to the next node, in which image capture is started and streamed 127. A next step can be to determine whether a visible light capturing device is connected 128. If a visible light image capturing device is not connected, the image acquisition process is complete 130. If a visible light image capturing device is connected, a visible light image is captured and saved 129 and then the image acquisition process is complete 130. A static image at a given wavelength can comprise a single image or multiple static images that are processed to generate a single static image. The static image can be obtained from a single chosen static image at a given counter or frame number or an average across a given set, or all counter or frame numbers.

A fourth module can comprise interactive tools for image processing including hemodynamic analysis, co-registration, and wound size analysis. The detected NIR light from two wavelengths can be used to determine changes (Δ) in HbO and HbR at every pixel of the NIR image using following formulas:

$$\Delta[HbO] = \frac{\varepsilon_{HbR}^{\lambda_1} \Delta OD^{\lambda_2} - \varepsilon_{HbR}^{\lambda_2} \Delta OD^{\lambda_1}}{(\varepsilon_{HbR}^{\lambda_1} \varepsilon_{HbO}^{\lambda_2} - \varepsilon_{HbR}^{\lambda_2} \varepsilon_{HbO}^{\lambda_1})L} \quad (1)$$

$$\Delta[HbR] = \frac{\varepsilon_{HbO}^{\lambda_2} \Delta OD^{\lambda_1} - \varepsilon_{HbO}^{\lambda_1} \Delta OD^{\lambda_2}}{(\varepsilon_{HbR}^{\lambda_1} \varepsilon_{HbO}^{\lambda_2} - \varepsilon_{HbR}^{\lambda_2} \varepsilon_{HbO}^{\lambda_1})L} \quad (2)$$

in which L is a pathlength factor (calibrated), ε is a molar extinction coefficient of HbO or HbR at $\lambda_1$ or $\lambda_2$ (between 650 nm and 1000 nm), and ΔOD is a change in an optical density (which is additionally wavelength dependent). Additionally, in certain embodiments of the subject invention, dark noise and effect of ambient light can be accounted for during hemodynamic analysis.

In certain embodiments, analysis of visible light images including digital color images, and oxygenation parameters can be achieved by leveraging image segmentation based algorithms. Image segmentation algorithms can use both contrast and texture information to perform automated or semi-automated segmentation. Segmentation techniques can include graph cuts, region growth, and/or other segmentation techniques used in general for image segmentation. A cut can be a partition that separates an image into two segments. Graph cut techniques can be a useful tool for accurately segmenting any type of image, which can result in a global solution since the technique is independent of the chosen initial center point. The algorithms can exploit similar gray values of closely situated pixels. After removing background noise, graph cut segmentation can reveal wound boundaries based on tissue oxygenation.

Region growing is a region-based or pixel-based algorithm for image segmentation, a pixel-based technique in which initial seed points can be manually selected by the user. The difference between intensity value of a pixel and mean intensity value of the user-specified region can be computed to determine the similarity level between neighboring pixels and the new pixel, called maximum intensity distance. Therefore, this algorithm can leverage a human expert's knowledge through user input of seed locations for the wound, and outperform user independent algorithms that are purely dependent upon computer based detection of visual cues found on the images.

Figure 7:
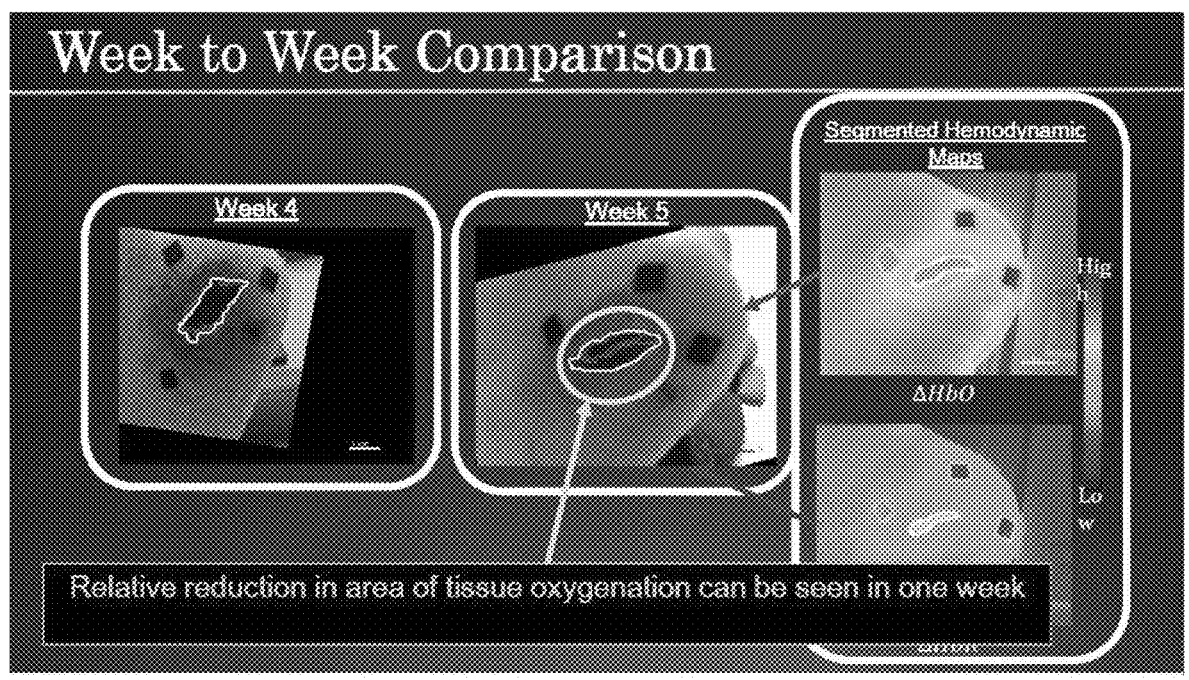
FIG. 7 shows images of a week to week comparison of wound healing according to an embodiment of the subject invention, in which the demarcated regions of changed hemoglobin is overlaid (or co-registered) onto the white light (or color) images of the wound.
Figure 8:
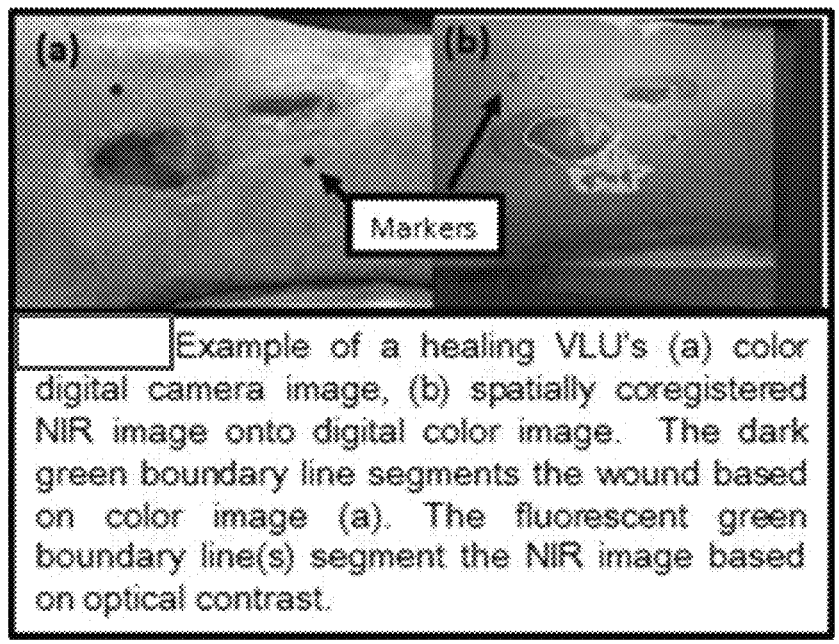
FIG. 8 shows an image of a VLU in which color and diffuse reflected NIR images are spatially co-registered according to an embodiment of the subject invention.
Figure 9:
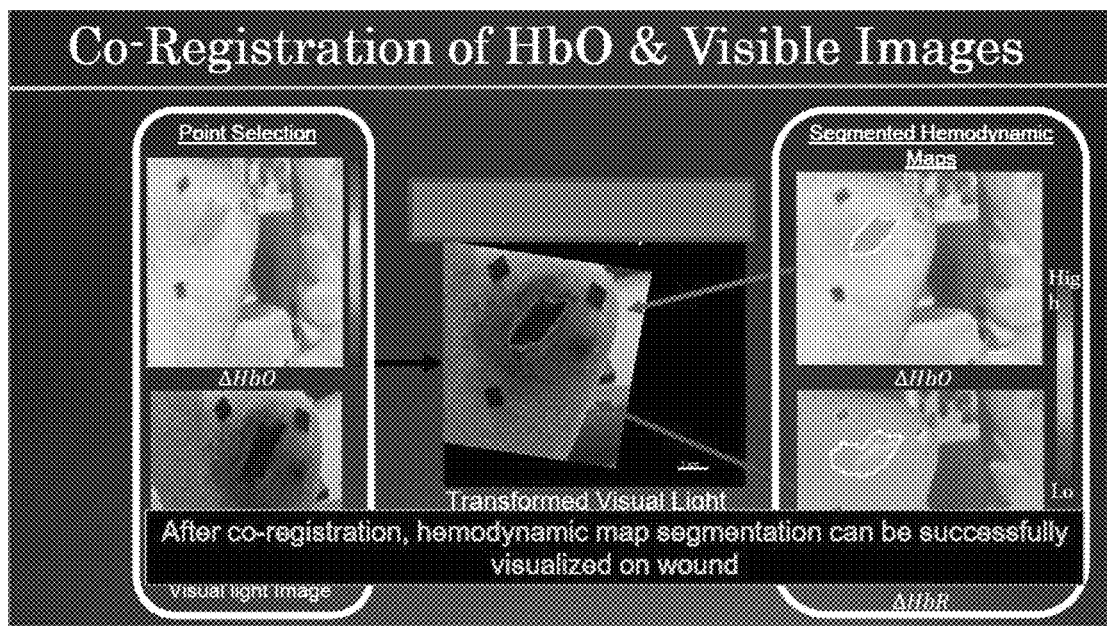
FIG. 9 shows an image of a co-registered HbO and visible image according to an embodiment of the subject invention.

In certain embodiments, two dimensional spatial maps of each oxygenation parameter (e.g., HbO, HbR, HbT, or any related parameter obtained from multi-wavelength NIR data) can be spatially co-registered onto visible light images, including digital color images of the wound or tissue of interest. Multi-map co-segmentation algorithms can be employed to differentiate healing vs. non-healing regions (for example, from demarcated wound boundaries and areas of changed blood flow, with or without demarcation). Spatial segmentation can facilitate demarcation of regions of interest and detection of their corresponding size changes during a treatment period, as seen in FIG. 7. As seen in FIG. 7, the segmented and demarcated regions of changed ΔHbO and ΔHbR were overlaid (or -spatially co-registered) onto the visible light images of the wound for a weekly comparison of observable wound's color images and sub-surface tissue oxygenation maps as demarcated boundaries. By co-registering multiple images, the wound regions segmented from images of different modalities (visible & MR imaging) can provide information regarding the progression of tissue oxygenation in and around the wound during its healing process. Wound images (i.e., color and NIR image) can have 2-3 reference markers of known size, enabling a co-registration algorithm to use shape, intensity contrast, texture, marker location and size to refine registration accuracy. In another embodiment, FIG. 8 shows an image of a VLU in which color and diffuse reflected NIR images are spatially co-registered. Color images obtained using a spatially separated endoscopic camera, can cause inaccurate co-registration of the two images, due to inability to obtain the same field of view. Embodiments of the subject invention, can be configured to acquire multi-wavelength NIR and color images, reduced overall imaging time and obtain the same field of view, orientation and distance from the wound, to facilitate accurate co-registration. FIG. 9 shows an image of co-registered HbO and visible image.

Figure 11:
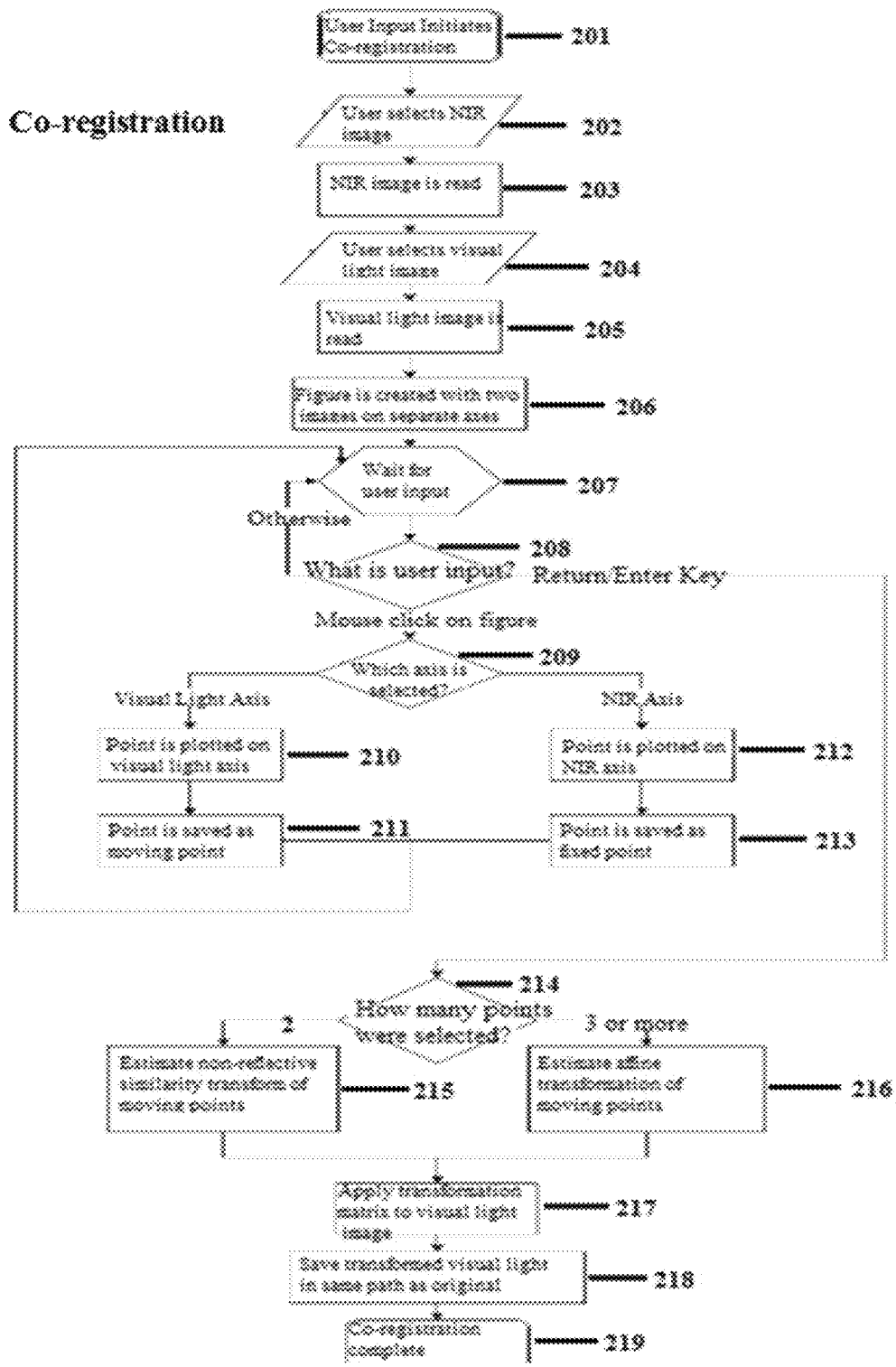
FIG. 11 shows a flow cart illustrating the process of co-registration according to an embodiment of the subject invention.

Hemodynamic analysis using 2 or 2 or more NIR wavelengths can be implemented using similar approach. Adding ΔHbO and ΔHbR gives ΔHbT (changes in total hemoglobin), and ΔHbO: ΔHbT estimates the $StO_2$ (saturated oxygen concentration). Second derivatives of either of the above parameters (i.e., ΔHbO, ΔHbR and/or ΔHbT) may also be estimated as part of hemodynamic analysis. Another feature of the fourth module can be interactive widgets or graphical icons that allow a user to implement spatial co-registration. The color and processed NIR images (i.e. hemodynamic maps) will be co-registered (overlaid) and can use reference markers for point selection in the transformation matrices. The differences in the visible light image capturing device and MR image capturing device's resolution can be accounted for via re-scaling the pixel areas through image processing techniques. The color and NIR images (at each imaged wavelength) can be co-registered for a visual comparison of a target (i.e., wound) size a n d hemodynamic maps, or the demarcated regions of changed oxygenation parameter(s), at and around the target during the imaging process. FIG. 11 is a flow chart illustrating the process of co-registration according to an embodiment of the subject invention. Within the state diagram, each state corresponds to a node. Each path is identified by an arrow, in which a path flows from one state to another state. In certain embodiments of the subject invention, the process begins when a user initiates co-registration 201. In other embodiments of the subject invention, the process of co-registration can be configured to begin automatically. A user can select an NIR image 202, whereupon the selected NIR image is read 203. After the user selects an MR image, the user can select a visible light image 204, whereupon the light image is read 205. In other embodiments of the subject invention, a visible light image can be selected prior to an NIR image. The system can then wait for user input 207. The path is directed to the user to choice of either: (1) delay entering an input, (2) select a figure, or (3) select hitting the return or enter key 208. If the user delays making a decision, the path can be directed towards a waiting state for the user to make a decision 207. If a user chooses to select an image, the system determines which axis has been selected 209. If the visible light axis is chosen, a point can be plotted on the visible light axis 210. The next state can comprise the point being saved as a moving point 211. If the NIR axis is chosen, a point can plotted on the NIR axis 212 and the point is saved as a fixed point 213. Afterwards, whether a user chose the visible light axis or the NIR axis, the path is directed back to waiting for user input 207. If the user chooses to hit the enter or return key, the path can be directed to a determination of how many points were selected 214. If two points are selected, the system can estimate a non-reflective similarity transform on the moving points 215. If three or more points are selected, the system estimates the affine transformation of the moving points 216. Upon completion of estimation, the paths of both states 215, 216 can be directed to applying a transformation matrix to the visible light image 217. After which, the transformed visible light image can be saved in the same path as the original visible light image 219, which completes the co-registration process.

Figure 12A:
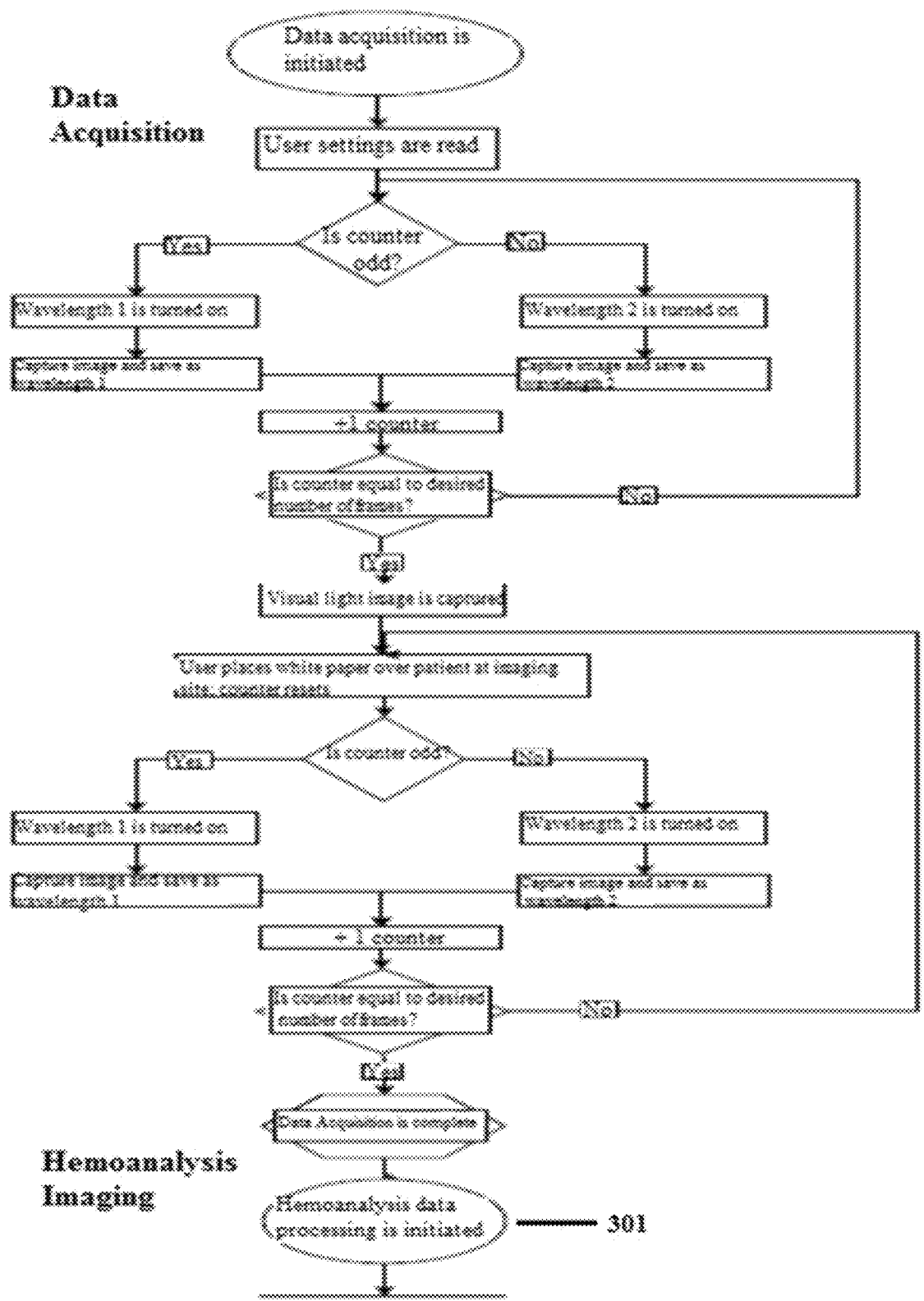
FIGS. 12A-12C show a state diagram illustrating the data acquisition process, hemoanalysis imaging, and co-registration process according to an embodiment of the subject invention.
Figure 12B:
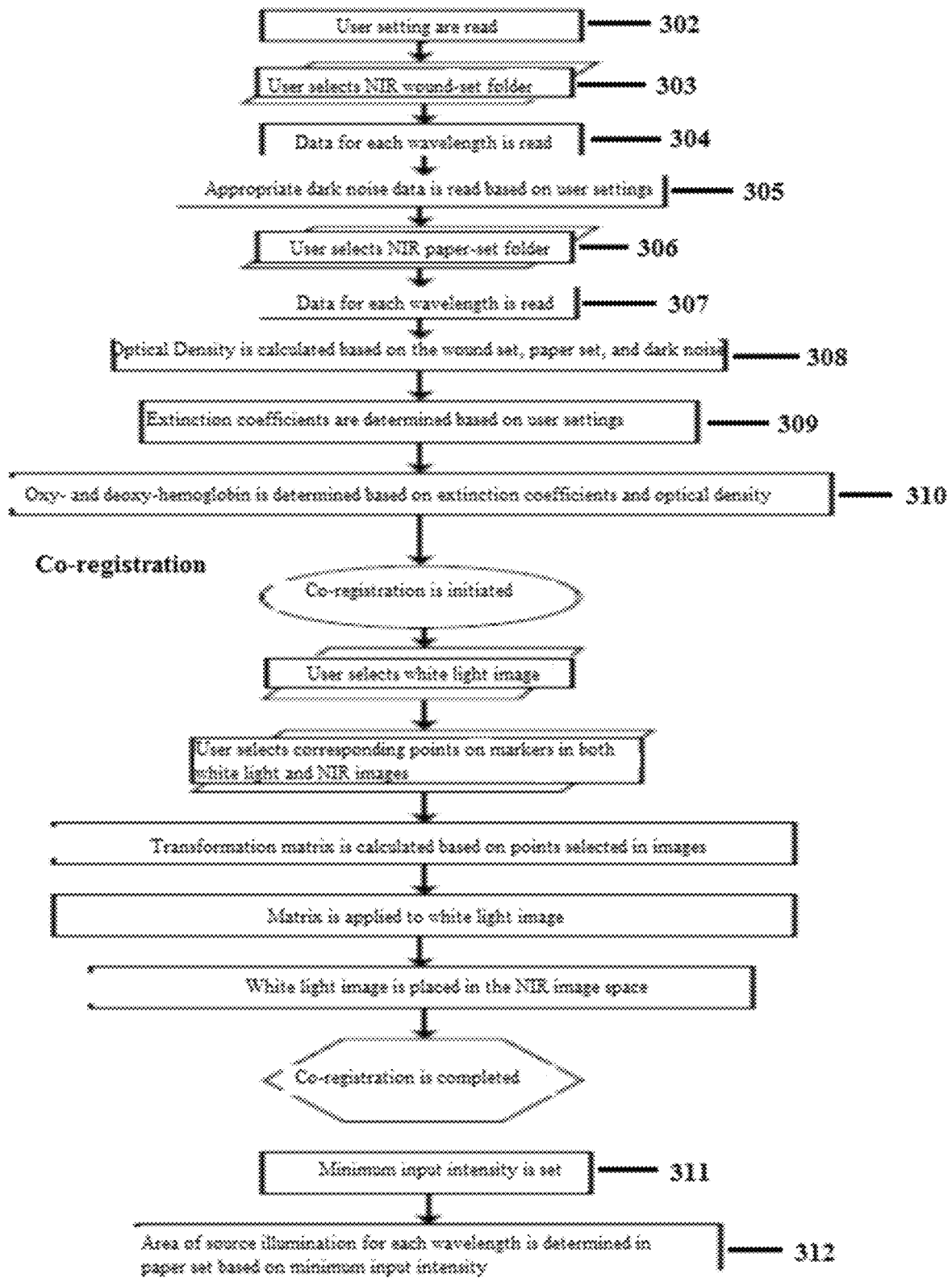
Figure 12C:
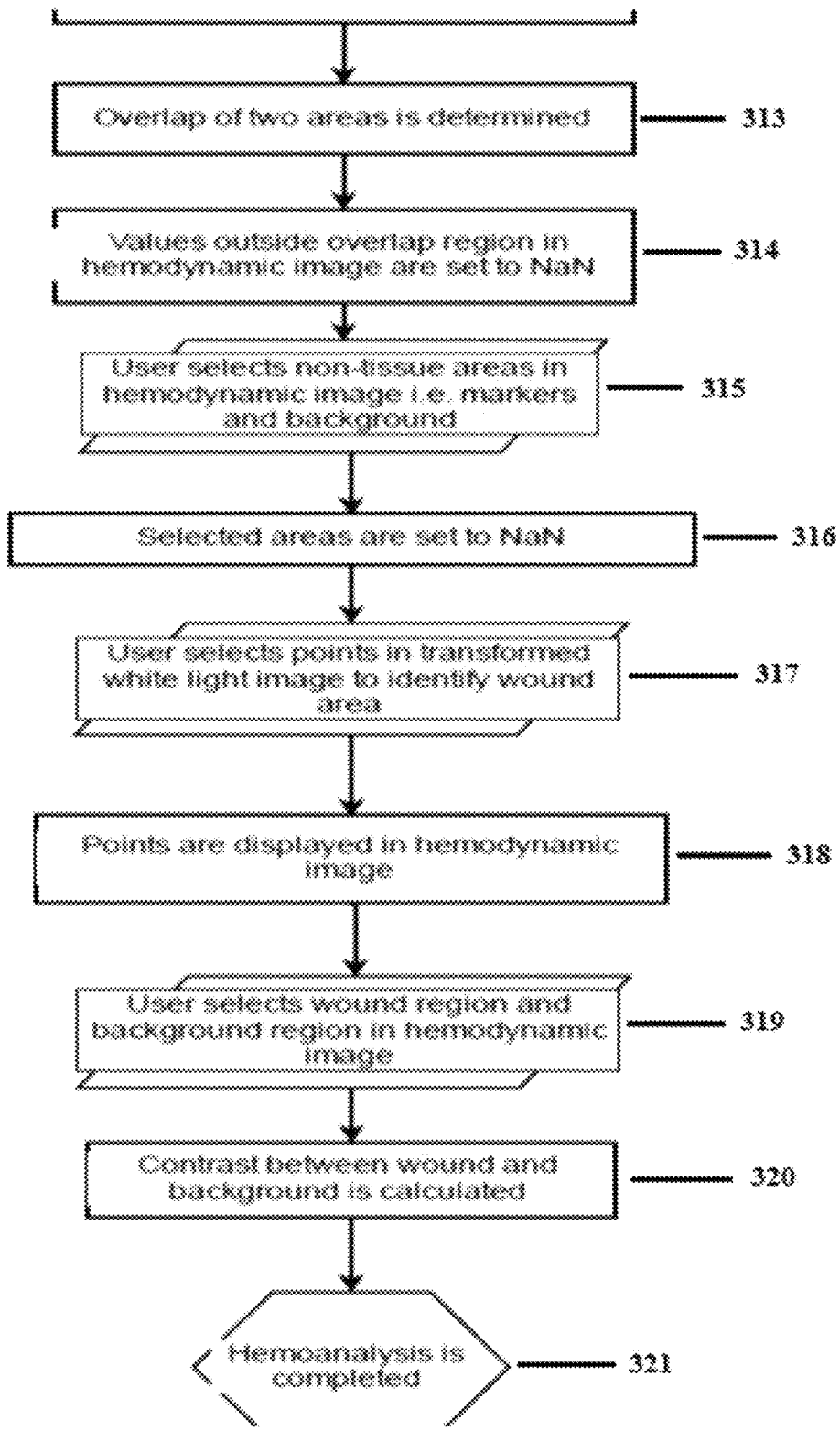

In another embodiment of the subject invention, the process flow can begin with (1) data acquisition, followed by (2) hemoanalysis imaging, and can be completed with (3) co-registration. FIGS. 12A-12C show the three parts of a flow chart illustrating the process of data acquisition, hemoanalysis imaging, and co-registration according to an embodiment of the subject invention. Within the state diagram, each state corresponds to a node. Each path is identified by an arrow, in which a path flows from one state to another state. In a certain embodiment of the subject invention, hemoanalysis is initiated after data acquisition is complete 301. A first step can be to read any user settings 302. A user can then select an NIR wound-set folder 303. Data from each image from each wavelength can be read 304. The path can be directed to the next state in which appropriate dark noise data can be read based upon user settings 305. A user can next select an MR paper-set folder 306. Data can be the read for each image taken at each wavelength 307. In a following state, optical density can be calculated based on the wound set, paper set, and ark noise data 308. In a following state, extinction coefficients can be determined based upon user settings 309. Changes in oxy and deoxy-hemoglobin (or other oxygenation parameters such as total hemoglobin and/or saturated oxygen) can be determined based upon extinction coefficients and optical density 310, upon which co-registration can be initiated. Upon completion of co-registration a minimum input intensity can be set 311. An area of source illumination for each wavelength can be determined in a paper set based upon a minimum input intensity 312. A possible next state can be to set values for two areas of the NIR and visible light images to determine any overlap 313. Values for outside of an overlap region can be set to a data type of not a number (NaN) 314. A user can select non-tissue areas in a hemodynamic image (i.e., markers and background) 315. Selected non-tissue areas can be assigned NaN data types 316. A user can select points in a transformed white light image to identify the wound area 317. These user selected points from the transformed white light image can be displayed in a hemodynamic image 319. A contrast between the wound and background image can be calculated 320, upon which hemoanalysis is completed 321.

Though systems and methods have been discussed with respect to wound care, embodiments are not limited thereto. Systems and methods of embodiments of the subject invention can be used for many other applications, including but not limited to pressure ulcers, diabetic foot ulcers, radiation-induced dermatitis for head/neck and breast cancer cases, and early cancer screening (e.g., breast cancer early screening).

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. A system for scanning near infrared (NIR) and visible light images, the system comprising:

an image capturing device configured to capture a visible light image (e.g., a visible light image comprising a digital color or white light image);

an image capturing device configured to capture a near infrared (NIR) image;

a portable, handheld housing unit configured to contain the visible light image capturing device and the NIR image capturing device;

a light source configured to illuminate a target area and in operable communication with (e.g., connected to) the housing unit;

a plurality of drivers configured to control the light source;

a processor; and a machine-readable medium comprising machine-executable instructions stored thereon, in operable communication with the processor.

Embodiment 2. The system of embodiment 1, in which the processor is configured to generate a near real time hemodynamic signal, and in which the processor is configured to detect a dimensional measurements of a target tissue wound.

Embodiment 3. The system of any of embodiments 1-2, in which the visible image capturing device and the NIR image capturing device are configured to capture the same or similar field of view.

Embodiment 4. The system of any of embodiments 1-3, in which the system is configured to use light in the visible or near infrared light wavelengths to monitor changes in the blood flow in terms of oxy- (HbO), deoxyhemoglobin (HbR), oxygen saturation (StO2), total hemoglobin (HbT), other derived oxygenation parameters, and/or tissue perfusion of the wounds Or tissue of interest.

Embodiment 5. The system according to any of embodiments 1-4, in which the system can detect MR light from at least two wavelengths to determine changes (Δ) in HbO and HbR at every pixel of the NIR image using following formulas:

$$\Delta[HbO] = \frac{\varepsilon_{HbR}^{\lambda_1}\Delta OD^{\lambda_2} - \varepsilon_{HbR}^{\lambda_2}\Delta OD^{\lambda_1}}{\left(\varepsilon_{HbR}^{\lambda_1}\varepsilon_{HbO}^{\lambda_2} - \varepsilon_{HbR}^{\lambda_2}\varepsilon_{HbO}^{\lambda_1}\right)L} \quad (1)$$

$$\Delta[HbR] = \frac{\varepsilon_{HbO}^{\lambda_2}\Delta OD^{\lambda_1} - \varepsilon_{HbO}^{\lambda_1}\Delta OD^{\lambda_2}}{\left(\varepsilon_{HbR}^{\lambda_1}\varepsilon_{HbO}^{\lambda_2} - \varepsilon_{HbR}^{\lambda_2}\varepsilon_{HbO}^{\lambda_1}\right)L} \quad (2)$$

where L is a pathlength factor (calibrated), ε is a molar extinction coefficient of HbO or HbR at $\lambda_1$ or $\lambda_2$ (between 650 nm and 1000 nm), and ΔOD is a change in an optical density (which is additionally wavelength dependent).

Embodiment 6. The system of any of embodiments 1-5, in which the light source is configured to emit light of at least one wavelength.

Embodiment 7. The system of any of the embodiments 1-6, in which the light source is configured to emit light at a first wavelength and sequentially or simultaneously to light at a second wavelength.

Embodiment 8. The system of any of embodiments 1-7, in which the NIR image capturing device is configured to capture the NIR image of at least two different wavelengths.

Embodiment 9. The system of any of embodiments 1-8, in which the processor is configured to detect and differentiate MR images of at least two wavelengths.

Embodiment 10. The system of any of embodiments 1-9, in which the processor is configured to detect a diffuse reflectance signal from at least 2 NIR wavelengths and generate a hemodynamic signal.

Embodiment 11. The system of any of embodiments 1-10, in which the processor is configured to capture a plurality of visible light images (for example, digital color or white light images) in the form of static images or a video.

Embodiment 12. The system of any of embodiments 1-11, in which the processor is configured to capture a plurality of NIR images in the form of a static images or a video.

Embodiment 13. The system of any of embodiments 1-12, in which the processor is configured to capture the NIR images, capture the visible light images, generate hemodynamic maps, overlay or co-register a hemodynamic map (for example, a HbO, HbR, or HbT map) onto the visible light images, including a digital color or white light image, to form a static single image.

Embodiment 14. The system of embodiments 1-13, in which the pressor is configured to capture an NIR image overlay or co-register the NIR image onto a visible light image.

Embodiment 15 The system of any of embodiments 1-14 in which the processor is configured to capture the MR images, capture the visible light images, generate hemodynamic maps, analyze tissue or wound measurements using image segmentation algorithms, generate a spatially co-registered image.

Embodiment 16. The system of any of embodiments 1-15, in which the processor is configured to capture a plurality of NIR images, capture a plurality of visible light images, including digital color or white light images, and overlay the images to generate a single video.

Embodiment 17. The system of any of embodiments 1-16, in which the processor is configured to capture a plurality of NIR images, capture a plurality of visible light images, including digital color or white light images, and analyze tissue or wound images using image segmentation algorithms, and generate spatially co-registered images in the form of a video.

Embodiment 18. The system of any of embodiments 1-19, in which the system further comprises a graphical user interface (GUI).

Embodiment 19. The system of embodiment 18, in which the GUI comprises a plurality of modules, in which the modules permit a user to interact with the system to perform tasks, in which the task comprise: initialization of the system, access to a patient's medical information, data acquisition, image processing, hemodynamic analysis, co-registration, and adjusting general camera settings.

Embodiment 20. The system of any of embodiments 1-19, further comprising wireless circuitry (for example, Bluetooth), such that the visible image capturing device, the NIR image capturing device and light source can wirelessly communicate with the processor and the machine readable medium.

Embodiment 21. The system of any of embodiments 1-20, in which the processor is configured to capture a single visible light image and provide a real time image in the form of a static image or a video.

Embodiment 22. The system of any of embodiments 1-21, in which the processor is configured to capture a single NIR image and provide a near real time image in the form of a static image or a video.

Embodiment 23. The system of any of embodiments 1-22, in which the processor is configured to remove a selected portion of the visible light image(s).

Embodiment 24. The system of any of embodiments 1-23, in which the processor is configured to remove a selected portion of the NIR image(s).

Embodiment 25. The system of any of embodiments 1-24, in which the processor is configured to detect and remove a noise signal and an effect of ambient light during image analysis.

Embodiment 26. The system of any of embodiments 1-25, in which the processor is configured to monitor the changes in the blood flow in terms of oxy- (HbO), deoxyhemoglobin (HbR), oxygen saturation (StO2), total hemoglobin (HbT), other derived oxygenation parameters (i.e. second derivatives) and/or tissue perfusion of the wounds.

Embodiment 27. The system of any of embodiments 1-26, in which the processor is configured to monitor changes in the measurement of a target tissue.

Embodiment 28. A device for scanning near infrared (NIR) and visible light images, the device comprising:

an image capturing device configured to capture a visible light image (e.g., a visible light image comprising a digital color or white light image);

an image capturing device configured to capture a near infrared red (NIR) image at a plurality of wavelengths;

a portable, handheld housing unit configured to contain the visible light image capturing device and the NIR image capturing device, in which the portable handheld housing unit comprises a front face, a right side face, and left side face, a back face, a top face and a bottom face, in which the visible light image capturing device and the NIR image capturing device are configured to capture the same or similar point of view;

a mounting clip connected to the housing unit on the bottom face and near the back face;

a light source to illuminate a target tissue and connected to the housing unit;

a processor; and a machine-readable medium comprising machine-executable instructions stored thereon, in operable communication with the processor.

Embodiment 29. The device of embodiment 28, in which light source is configured emit light of at least one wavelength.

Embodiment 30. The device of any of embodiment 28-29, in which the processor is configured to generate a near real time hemodynamic signal.

Embodiment 31. The device of any of embodiment 28-30, in which the processor is further configured to detect light of at least one wavelength.

Embodiment 32. The device of any of embodiment 28-31, in which the processor is configured to use image segmentation techniques to execute a size measurement of a target tissue.

Embodiment 33. The device of any of embodiment 28-32, in which the light source is connected to the top face of the housing unit and is near the front face.

Embodiment 34. The device of any of embodiment 28-33, in which the light source is connected by a hinge to the top face of a housing unit and is near the front face.

Embodiment 35. A method scanning near infrared (NIR) and visible light images, the method comprising:

placing the device of any of embodiments 28-34 at a distance from a target tissue;

configuring the visible light image capturing device and the NIR image capturing device to have a same field of view onto the target tissue;

illuminating the target wound, with the light source, with at least one wavelength;

capturing a visible light image (e.g., a visible light image comprising a digital color or white light image) and an NIR image, of at least one wavelength, of the target tissue.

Embodiment 36. The method according to embodiment 35, in which the method further comprises detecting a NIR signal from each wavelength emitted from the light source; detecting a noise signal; selecting an unwanted region of the visible light image of the target wound; processing the visible light image and the NIR image to remove the unwanted regions and to remove the noise signal; producing a hemodynamic map; and processing the visible light image to determine size of wound.

Embodiment 37. The method according to any of embodiments 35-36, in which the method further comprises selecting corresponding marker points on the NIR image and the visible light image; generate a transformational mapping matrix based upon the selected points; and overlaying the NIR image, hemodynamic map, or segmented boundaries of NIR image or hemodynamic map onto the visible light image to produce a single image.

Embodiment 38. The method according to any of embodiments 35-37, in which the method further comprises selecting corresponding marker points on the NIR image and the visible light image; generate a transformational mapping matrix based upon the selected points; and using image segmentation techniques to overlay the NIR image, the hemodynamic map, and/or segmented boundaries of NIR image or hemodynamic map onto the visible light image to produce a single image.

Embodiment 39. The method according to any of embodiments 35-38, in which the method comprises capturing a plurality of the visible light images and a plurality the NIR images, and overlaying or co-registering the plurality of visible light and NIR images to produce and display a single video.

A greater understanding of the present invention and of its many advantages may be had from the following example, given by way of illustration. The following example is illustrative of some of the methods, applications, embodiments and variants of the present invention. The example is, of course, not to be considered as limiting the invention. Numerous changes and modifications can be made with respect to the invention.

EXAMPLE 1

Figures 4A, 4B:
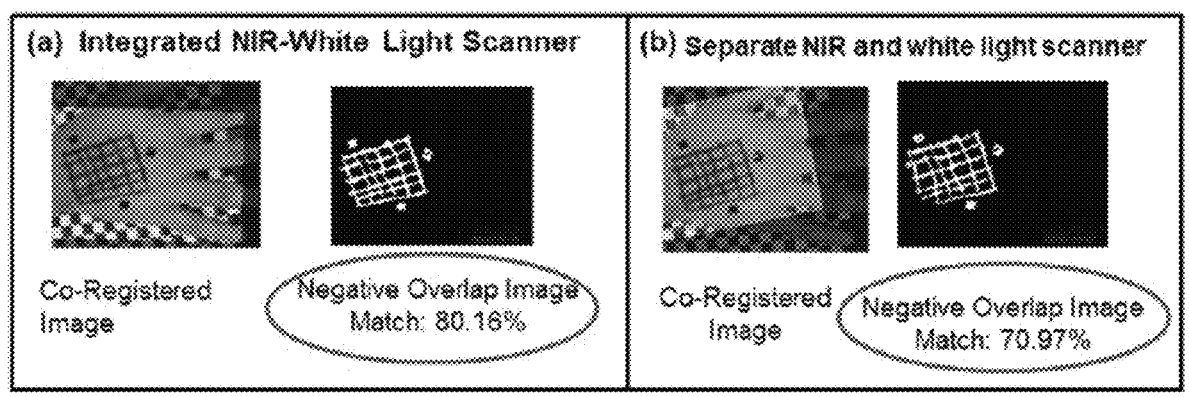
FIG. 4(a) shows a plot of a system's ability to overlay (co-register) an image according to an embodiment of the subject invention.
FIG. 4(b) shows a plot of a system's ability to overlay (co-register) an image according to an embodiment of the subject invention.

FIG. 4 is a sample plot from studies carried out to determine the ability of the integrated system to co-register images faster and with more accurately than a system that uses a near-infrared optical scanner with only NIR-imaging capability, and a separate endoscopic camera for white light images.

Use of two cameras in a lab setting (endoscopic for color image and CMOS camera for MR images) co-registered the color and NIR images with 70% accuracy, while involving 1 minute in positioning the endoscopic camera for similar orientation and FOV as the NIR-camera. A preliminary test using an integrated pinhole color camera onto the hand-held body of NIR camera co-registered the two images with over 80% accuracy, while involving no additional time in positioning the pinhole camera, as see in FIG. 4. Hence, an integrated color and NIR imaging device can improve co-registration accuracy, and also reducing the overall patient imaging time (entry to exit from clinical room), apart from providing two healing indicators (wound size and hemodynamic changes) using this device.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Jarbrink K, Ni G, Sonnergren H, Schmidtchen A, Pang C, Bajpai R, Car J, Prevelance and incidence of chronic wounds and related complications: a protocol for a systematic review. Systematic Reviews. 2016; 5:152-157.
2. https://www.alliedmarketresearch.com/wound-closure-wound-care-market
3. Alavi A, Sibbald R G, Philips T J, Miller O F, Margolis D J, Marston W, Woo K, Romanelli M, Kirsner R S, What's new: Management of venous leg ulcers—Approach to venous leg ulcers. J of American Academy of Dermatology. 2016; 74(4): 627639.
4. Steed D L, Attinger C, Colaizzi T, Crossland M, Franz M, Harkless L, Johnson A, Moosa H, Robson M, Serena T, Sheehan P, Veves A, Wiersma-Bryant L. Guidelines for the treatment of diabetic ulcers. Wound Repair Regen 2006; 14: 680-92.
5. Neidrauer M, Zubkov L, Weingarten M S, Pourrezaei K, Papazoglou E S. Near infrared wound monitor helps clinical assessment of diabetic foot ulcers. J Diabetes Sci Technol. 2010; 4(4): 792-798.
6. Weingarten M S, Neidrauer M, Mateo A, Mao X, McDaniel J E, Jenkins L, et al. Prediction of wound healing in human diabetic foot ulcers by diffuse near-infrared spectroscopy: A pilot study. Wound Rep Reg. 2010; 18:180-185.
7. Schreml S, Szeimies R M, Prantl L, KarrerS, Landthaler M, Babilas P. Oxygen in acute and chronic wound healing (Review article). British J of Dermatology. 2010 163:257-268.
8. Jung Y-J, Gonzalez J, Godavarty A, "Functional NIR imaging reconstruction based on spatio-temporal feature: Venous occlusion studies," Appl. Opt. 2015; 54(13): D82-D90.
9. Jung Y-J, Roman M, Carrasquilla J, Erickson S J, Godavarty A. Portable wide-field hand-held NIR scanner. SPIE Photonics West, A. Mahadevan-Jansen, T. Vo-Dinh, and W. S. Grundfest, eds.; 2013; 8527: 85720A-85720A-9.
10. Jung Y-J, Gonzalez J, Rodriguez S, Mejia M V, Clark G, Godavarty A. Anatomical Co-Registration using Spatio-Temporal Features of a Non-contact Near-Infrared Optical Scanner. Proc. of SPIE 8942; Dynamics and Fluctuations in Biomedical Photonics X I, 89420F; 26 Feb. 2014.
11. Jung Y-J, Mejia M V, Godavarty A. Spatio-temporal hemodynamic imaging using a non-contact NIR scanner. Biomedical Optics Conference Paper, OSA, BS3A; 26-30 Apr. 2014.
12. Godavarty A, Khandavilli Y, Jung Y-J, Rao PNS, "Non-contact optical imaging of healing and non-healing diabetic foot ulcers," SPIE BiOS, 931802-931802 (2015).
13. Godavarty A, Rao PNS, Khandavilli Y, Jung Y-J, "Diabetic wound imaging using a non-contact near-infrared scanner: A pilot study," J. of Diabetes Science and Technology 2015; 9(5):1158-59.
14. Lei J, Rodriguez S, Jayachandran M, Solis E, Gonzalez S, Perez-Clavijo F, Wigley S., Godavarty Quantitative wound healing studies using a portable, low-cost, hand-held near-infrared optical scanner: Preliminary sensitivity and specificity analysis. Proc. of SPIE 9699, Optics and Biophotonics in Low-Resource Settings II, 96990S (Mar. 7 2016); doi: 10.1117/12.2212070.
15. Dadkhah, X. Pang, E. Solis, R. Fang, A. Godavarty, "Wound size measurement of lower extremity ulcers using segmentation algorithms," Proc. SPIE 9703, Optical Biopsy XIV: Toward Real-Time Spectroscopic Imaging and Diagnosis, 97031D (Mar. 7, 2016); doi: 10.1117/12.2212046.
16. Pang X, Dadkhah A, Lei J, Solis E, Rodriguez S, Perez-Clavijo F, Wigley S, Fang R, Godavarty Near-infrared optical imaging and wound segmentation in lower extremity ulcers. OSA Technical Digest Paper jTu3A.43 (April 2016).
17. U.S. Patent Application Publication No. 2015/0190061.
18. U.S. Patent Application Publication No. 2014/0364743.
19. U.S. Patent Application Publication No. 2010/0190061.
20. U.S. Pat. No. 9,635,649.
21. U.S. Pat. No. 8,712,504.

What is claimed is:

1. A system for scanning near infrared (NIR) and visible light images, the system comprising:
    a visible image capturing device configured to capture a visible light image, the visible light image comprising a digital color or white light image;
    a near infrared image capturing device configured to capture a near infrared (NIR) image of at least one wavelength;
    a portable, handheld, housing unit in which the visible image capturing device and the NIR image capturing device are contained, the housing unit comprising an NIR image capturing device compartment in which the NIR image capturing device is contained and a visible image capturing device compartment in which the visible image capturing device is contained, the NIR image capturing device being physically separated from the visible image capturing device by a wall of the NIR image capturing device compartment;
    a light source configured to illuminate a target area and connected to the housing unit,
    a plurality of drivers configured to control the light source;
    a processor; and
    a machine-readable medium comprising machine-executable instructions stored thereon, in operable communication with the processor,
    the light source comprising a plurality of light emitting diodes (LEDs) configured to emit light waves of at least one wavelength,
    the processor being configured to detect at least one NIR signal at at least one wavelength and generate a hemodynamic signal,
    the processor being configured to detect dimensional measurements of a target tissue or wound, the NIR image capturing device being disposed in the housing unit such that it faces out of a front face of the housing unit, the light source being disposed on a top face of the housing unit through a hinge, such that an angle of illumination provided by the light source is adjustable via the hinge without moving the housing unit, the processor being configured to detect a plurality of NIR images at a plurality of wavelengths, detect a visible light image, generate a hemodynamic map, and co-register the hemodynamic map onto the visible light image to generate a spatially co-registered static single image, and the housing unit comprising a camera aperture access hole on a side face thereof different from the top face and the front face.

2. The system of claim 1, the visible image capturing device and the NIR image capturing device being configured to capture the same or similar field of view.

3. The system of claim 1, the processor being configured to use light in a visible or near infrared light wavelength to monitor changes in the blood flow in terms of oxy- (HbO), deoxyhemoglobin (HbR), oxygen saturation (StO2), total hemoglobin (HbT), related parameter obtained from the plurality of NIR signals at the plurality of wavelengths, and/or tissue perfusion of the wounds.

4. The system of claim 1, the system being configured to detect aNIR light signal from at least two wavelengths to determine changes (Δ) in HbO and HbR at every pixel of the NIR image using the following formulas:

$$\Delta[HbO] = \frac{\varepsilon_{HbR}^{\lambda_1} \Delta OD^{\lambda_2} - \varepsilon_{HbR}^{\lambda_2} \Delta OD^{\lambda_1}}{(\varepsilon_{HbR}^{\lambda_1} \varepsilon_{HbO}^{\lambda_2} - \varepsilon_{HbR}^{\lambda_2} \varepsilon_{HbO}^{\lambda_1})L} \quad (1)$$

$$\Delta[HbR] = \frac{\varepsilon_{HbO}^{\lambda_2} \Delta OD^{\lambda_1} - \varepsilon_{HbO}^{\lambda_1} \Delta OD^{\lambda_2}}{(\varepsilon_{HbR}^{\lambda_1} \varepsilon_{HbO}^{\lambda_2} - \varepsilon_{HbR}^{\lambda_2} \varepsilon_{HbO}^{\lambda_1})L} \quad (2)$$

where L is a pathlength factor, ε is a molar extinction coefficient of HbO or HbR at $\lambda_1$ or $\lambda_2$ between 650 nm and 1000 nm, and ΔOD is a change in an optical density.

5. The system of claim 1, the processor being configured to detect and differentiate NIR images of at least two different wavelengths.

6. The system of claim 1, the processor being configured to detect a diffuse reflectance signal and generate a hemodynamic signal from the plurality of NIR signals at the plurality of wavelengths.

7. The system of claim 1, the processor being configured to detect an NIR image, detect a visible light image, and co-register the NIR image onto the visible light image to generate a spatially co-registered static single image.

8. The system of claim 1, the processor being configured to apply image segmentation techniques to the visible light image and the hemodynamic map to measure the target wound or tissue.

9. The system of claim 1, the processor being configured to detect a plurality of NIR images, detect a plurality of visible light images, generate a plurality of hemodynamic maps and co-register the hemodynamic maps onto the visible light images to generate a single video.

10. The system of claim 1, further comprising a graphical user interface (GUI) comprising a plurality of modules, the modules permitting a user to interact with the system to perform tasks, the tasks comprising: initialization of the system; access to a patient's, medical information, data acquisition; image processing, hemodynamic analysis, co-registration, and adjusting general camera settings.

11. The system of claim 1, further comprising wireless circuitry, such that the visible image capturing device, the NIR image capturing device, and the light source can wirelessly communicate with the processor and the machine readable medium.

12. The system of claim 1, the processor being configured to detect a noise signal and an effect of ambient light during an image analysis.

13. The system of claim 1, the processor being configured to monitor changes in a blood flow in terms of oxy- (HbO), deoxyhemoglobin (HbR), oxygen saturation (StO2), total hemoglobin (HbT), or other related parameter derived from the plurality of NIR signals at the plurality of wavelengths, and/or tissue perfusion of the wounds.

14. A device for scanning near infrared (NIR) and visible light images, the device comprising:

a visible image capturing device configured to capture a visible light image, the visible light image comprising a digital color or white light image;

a near infrared (NIR) image capturing device configured to capture an NIR image of at least one wavelength;

a portable, handheld housing unit in which the visible light image capturing device and the NIR image capturing device are contained, the portable handheld housing unit comprising a front face, a right side face, a left side face, a back face, a top face, and a bottom face, and the visible light image capturing device and the NIR image capturing device being configured to capture the same or similar point of view;

a mounting clip connected to the housing unit on the bottom face and near the back face;

a light source configured to illuminate a target area and connected to the housing unit;

a processor; and a machine-readable medium comprising machine-executable instructions stored thereon, in operable communication with the processor, the light source being disposed on the top face of the housing unit and being near the front face;

the processor being configured to detect an NIR signal and generate a hemodynamic signal, the processor being further configured to detect at least one wavelength, the processor being configured to execute dimensional measurements of a target tissue or wound, the housing unit comprising an NIR image capturing device compartment in which the NIR image capturing device is contained and a visible image capturing device compartment in which the visible image capturing device is contained, the NIR image capturing device being physically separated from the visible image capturing device by a wall of the NIR image capturing device compartment, the NIR image capturing device being disposed on in the housing unit such that it faces out of the front face of the housing unit, the light source being disposed on the top face of the housing unit through a hinge, such that an angle of illumination provided by the light source is adjustable via the hinge without moving the housing unit, the processor being configured to detect a plurality of NIR images at a plurality of wavelengths, detect a visible light image, generate a hemodynamic map, and co-register the hemodynamic map onto the visible light image to generate a spatially co-registered static single image, and the housing unit comprising a camera aperture access hole on the right side face or the left side face thereof.

15. A method of scanning near infrared (NIR) and visible light images, the method comprising:
placing the device of claim 14 at a distance from a target tissue or wound;
configuring the visible light image capturing device and the NIR image capturing device to have a same field of view onto the target tissue;
illuminating the target wound, with the light source of at least one wavelength;
capturing at least one visible light image and at least one NIR image of the target tissue;
detecting an NIR signal from each wavelength emitted from the light source;
detecting a noise signal;
selecting an unwanted region of the visible light image of the target tissue;
processing the visible light image and the NIR image to remove the unwanted region and to remove the noise signal;
generating a hemodynamic map;
detecting a size measurement of the target tissue or wound;
selecting corresponding marker points on the NIR image and the visible light image;
generating a transformational mapping matrix based upon the selected points; and
co-registering the hemodynamic map onto the visible light image based upon the transformational matrix to produce a single image.

16. The method to of claim 15, the processor being configured to segment the NIR image and the white light image, execute image segmentation algorithms, demarcate a boundary of a region of interest on either the NIR image or visible light image, or both images, and calculate an area of the demarcated region.

17. The method of claim 16, further comprising capturing a plurality of visible light images and a plurality of NIR images, and co-registering the plurality of visible light and NIR images to produce a single video, and
the processor being further configured to further co-register the demarcated boundaries obtained from the NIR image onto the visible light image.

18. The method according to claim 17, the processor being further configured to co-register both the NIR and visible light boundaries onto the visible light image.

19. The method according to claim 17, the processor being further configured to co-register both the NIR and visible light boundaries onto the NIR image.

* * * * *